United States Patent
Singh

(10) Patent No.: US 8,435,233 B2
(45) Date of Patent: May 7, 2013

(54) METHOD AND A SYSTEM FOR LASER PHOTOABLATION WITHIN A LENS

(76) Inventor: Ajoy I. Singh, Maharashtra (IN)

( * ) Notice: Subject to any disclaimer, the term of this patent is extended or adjusted under 35 U.S.C. 154(b) by 729 days.

(21) Appl. No.: 12/599,093

(22) PCT Filed: Apr. 15, 2008

(86) PCT No.: PCT/IN2008/000244
§ 371 (c)(1),
(2), (4) Date: Nov. 6, 2009

(87) PCT Pub. No.: WO2009/007990
PCT Pub. Date: Jan. 15, 2009

(65) Prior Publication Data
US 2010/0312231 A1    Dec. 9, 2010

(30) Foreign Application Priority Data

May 7, 2007    (IN) .......................................... 870/07

(51) Int. Cl.
*A61B 18/18*    (2006.01)
(52) U.S. Cl.
USPC .................................... 606/5; 606/11; 606/19

(58) Field of Classification Search .................. 606/4, 5, 606/10, 11, 107, 17–19; 128/898
See application file for complete search history.

(56) References Cited

U.S. PATENT DOCUMENTS

| | | | | |
|---|---|---|---|---|
| 3,653,384 A * | 4/1972 | Swope | ............................ | 606/18 |
| 5,722,952 A * | 3/1998 | Schachar | ...................... | 604/506 |
| 6,322,556 B1 | 11/2001 | Gwon et al. | | |
| 2002/0103478 A1* | 8/2002 | Gwon et al. | ...................... | 606/4 |
| 2010/0076417 A1* | 3/2010 | Suckewer et al. | ................. | 606/4 |

OTHER PUBLICATIONS

International Search Report: PCT/IN08/00244, Mar. 30, 2009.

* cited by examiner

*Primary Examiner* — Huy K Mai
(74) *Attorney, Agent, or Firm* — Ladas & Parry LLP

(57) ABSTRACT

A method for ablating a presbyopic lens for restoring accommodation in human eye and a system thereof wherein a laser beam is directed obliquely to carry out multiple photoablations in circular way within the lens behind the iris and preferably near the edge or equator of the lens and/or in the vicinity of zonules to re-establish accommodation of the lens lost due to presbyopia.

27 Claims, 6 Drawing Sheets

Section B-B

METHOD AND A SYSTEM FOR LASER PHOTOABLATION WITHIN A LENS

FIELD OF THE INVENTION

The present invention relates to opthalmology, more particularly to a method and a system to rectify/correct a vision defect/problem such as Presbyopia by means of laser photoablation within lens.

BACKGROUND AND PRIOR ART OF THE INVENTION

Human eye is essentially made up of three basic layers of tissue divided into three chambers as shown in FIG. 1. The sclera (12) surrounds the lens (3) except at the cornea (1), which is the transparent tissue and the exterior surface of the eye through which light first enters the eye. The iris (2) is a coloured, contractible membrane that controls the amount of light entering the eye by changing the size of the circular aperture at its center (the pupil). The ocular or crystalline lens (3) (herein after referred to as lens) is located just posterior to the iris (2). The lens comprises transparent gel-like proteins in a transparent capsule bag (not shown). Generally the lens changes shape through the action of the ciliary muscle (8) to allow for focusing of a visual image. A neural feedback mechanism from the brain allows the ciliary muscle (8), acting through the attachment of the zonules (11), to change the shape of the ocular lens. Generally, sight occurs when light enters the eye through the cornea (1) and pupil, then proceeds past the ocular lens (3) through the vitreous (10) along the visual axis (4) (herein after referred to as central axis of the lens), strikes the retina (5) at the back of the eye, forming an image at the macula (6) that is transferred by the optic nerve (7) to the brain. The space between the cornea and the retina is filled with a liquid called the aqueous in the anterior chamber (9) and the vitreous (10), a gel-like, clear substance posterior to the lens.

Usually, the eye converges light using two primary elements, the cornea and lens, onto the retina for detailed vision. 75% of the total 60 diopter focusing power of the eye is provided by the first element i.e. the convex outer surface of the cornea. The remaining 25% is provided by the crystalline lens, the second element.

The effective focal length of the human eye must be adjusted to keep the image of the object focused as sharply as possible on the retina/macula. This change in effective focal length is known as accommodation and is accomplished in the eye by varying the shape of the crystalline lens. This is necessary for the human eye to have clear vision of objects at different distances. Generally speaking, in the unaccommodated normal vision, the curvature of the lens is such that distant objects are sharply imaged on the retina/macula. In the unaccommodated eye, close objects are not sharply focused on the retina/macula and their images lie behind the retinal surface. In order to visualize a near object clearly, the curvature of the crystalline lens is increased, thereby increasing its refractive power and causing the image of the near object to fall on the retina/macula.

The lens is a bi-convex structure suspended by ligamentous zonules attached to an annular ciliary muscle. While the lens contributes only 25% of the focusing power, the primary purpose is to allow proper and perfect focusing of divergent light reflected from near objects as well as from far objects. This ability to focus on far way objects as well as to focus on near objects by change in dimensions of the lens is called accommodation.

Lens fibers grow through out the life by the elongation and differentiation of epithelial cells circumferentially at the equator of lens, which results in internalization of previously, formed protein fibers. The net effect is that the older protein fibers are always found towards the nucleus and the younger protein fibers towards the cortex.

Presbyopia is attributed to continued proliferation of lamellar lens cells. As the lens ages, it becomes less elastic due to change in the lens's curvature from continual growth and therefore its ability to change its curvature in response to the contraction and relaxation of ciliary muscles is reduced/inhibited and results in vision defects such as but not limited to presbyopia with age. Presbyopia also causes circumlental crowding in the sub-cialiary region of the eye including crowding of the zonular fibers as show in FIG. 2 along resulting in loss in power of the cialary muscles.

Therefore, restoration of accommodation ability of lens has always been a topic of research. Bifocal and other multifocal spectacles and contact lens more commonly use to solve the focal problem of presbyopia. A common disadvantage of these devices is that the poorly focused portions of the image reduce the contrast of the focused part of the image.

Other method included a phaco-ersatz procedure to remove a lens from the lens capsule of an eye and a liquid is then introduced into the lens capsule, followed by inserting a supplemental endo-capsular lens into the lens capsule.

As noted from the prior art, U.S. Pat. No. 6,322,556 provides a method for selective removal of ocular lens tissue of human eye for the correction of vision defects including myopia, hyperopia or presbyopia by means of laser ablation of such a selected region. As per the preferred embodiment of the said U S patent the more centrally located older cortical and/or nuclear fibers be ablated since the width of the nucleus remains relatively constant with age, whereas that of cortex increases.

So also the said patent emphasize that the reduction in thickness of lens is responsible to restore accommodation. Further, there is possibility of exposure of the retina near the macula or macula to the laser beam due to leaking of laser beam through the lens during the ablation process, which may harm the retina near macula.

However, in respect of photo ablation of the lens, it should be appreciated that the reprofiling of lens by reducing the thickness of lens is not the determinative factor for restoration of accommodation. Therefore, to enhance the ability of the ciliary muscle to constrict and relax via zonular ligaments is the topic of research for the scholars.

Therefore there is a need to provide a method and system for photoablation of tissues/fibers within the lens for correcting vision problems, particularly, associated with presbyopia by substantially reducing damage to the lens and other parts of eye.

SUMMARY OF THE INVENTION

An object of present invention is to provide a method and a system to reduce the coronal diameter of the lens for enhancement/improvement of the ability of the ciliary muscle to constrict and relax the lens capsule via zonular ligaments.

The present invention provides a method for restoring accommodation in human eye by modifying the structure of ocular lens. The said method comprises steps of: surveying a lens to be treated; establishing accommodation amplitude for the lens; estimating actual accommodation amplitude for the lens and determining the volume of the lens proteins to be photoablated; dividing the lens into parallel coronal planes; locating a zone for photoablation within the lens behind the iris; selecting a coronal plane for photoablation; directing incidental laser beam obliquely at an angle predetermined angle towards the coronal plane behind the iris to bring about spot photoablation within the selected zones behind the iris; and performing plurality of spot photoablation in substantially circular way on the coronal plane behind the iris within the selected zone thereby reducing the coronal diameter and thickness at sub-equatorial region of the lens causing reduction in circumlental crowding in the sub-cialiary region of the eye including crowding of zonular fibers resulting tensing of zonular fibres thereby re-establishing accommodation in the eye of the ocular lens.

The present invention also provides a system for performing photoablation of the lens for accommodation of a lens for the above method. The system according to the present invention comprises: a means for surveying the lens and any anterior parts thereof for establishing and estimating actual accommodation amplitude for an lens to be treated and to select zones for photoablation within the lens behind the iris; a laser system for ablating within the lens; a means for monitoring and controlling the photoablation process in real time; and a means to direct the laser beam adapted rotatably on the laser system for directing emitted incidentally by the laser system obliquely at an angle predetermined angle with the central axis within the lens behind the iris for photo-ablating the selected zone behind the iris to re-establish accommodation of the ocular lens in the eye.

The present invention also provides a mean to direct a laser beam to be adapted on a laser system of photoablation system. The means to direct laser beam comprises an articulated arm tube adapted rotatably about an axis of laser emitting source of the laser system; and at least two mirrors adapted periscopically in the said tube wherein first mirror receives the incident laser beam emitted by the laser source and directs towards second mirror, which reflect the laser beam obliquely towards the zone at an angle predetermined angle with the central axis.

BRIEF DESCRIPTION OF DRAWINGS

To illustrate the invention, a preferred embodiment thereof will now be described with reference to the accompanying drawings (which in no way restrict the scope of the invention and are for the purpose of illustration only) in which.

DETAILED DESCRIPTION OF THE INVENTION

In preferred general term, the present invention provides a method for ablating a presbyopic lens for restoring accommodation in human eye and a system thereof wherein a laser beam is directed obliquely to carry out multiple photoablations within the lens behind the iris and preferably near the edge or equator of the lens and/or in the vicinity of zonules to re-establish accommodation of the lens lost due to presbyopia. The laser beam according to the present invention has short duration and high-energy pulse to convert lens-protein into plasma.

Figure 3:
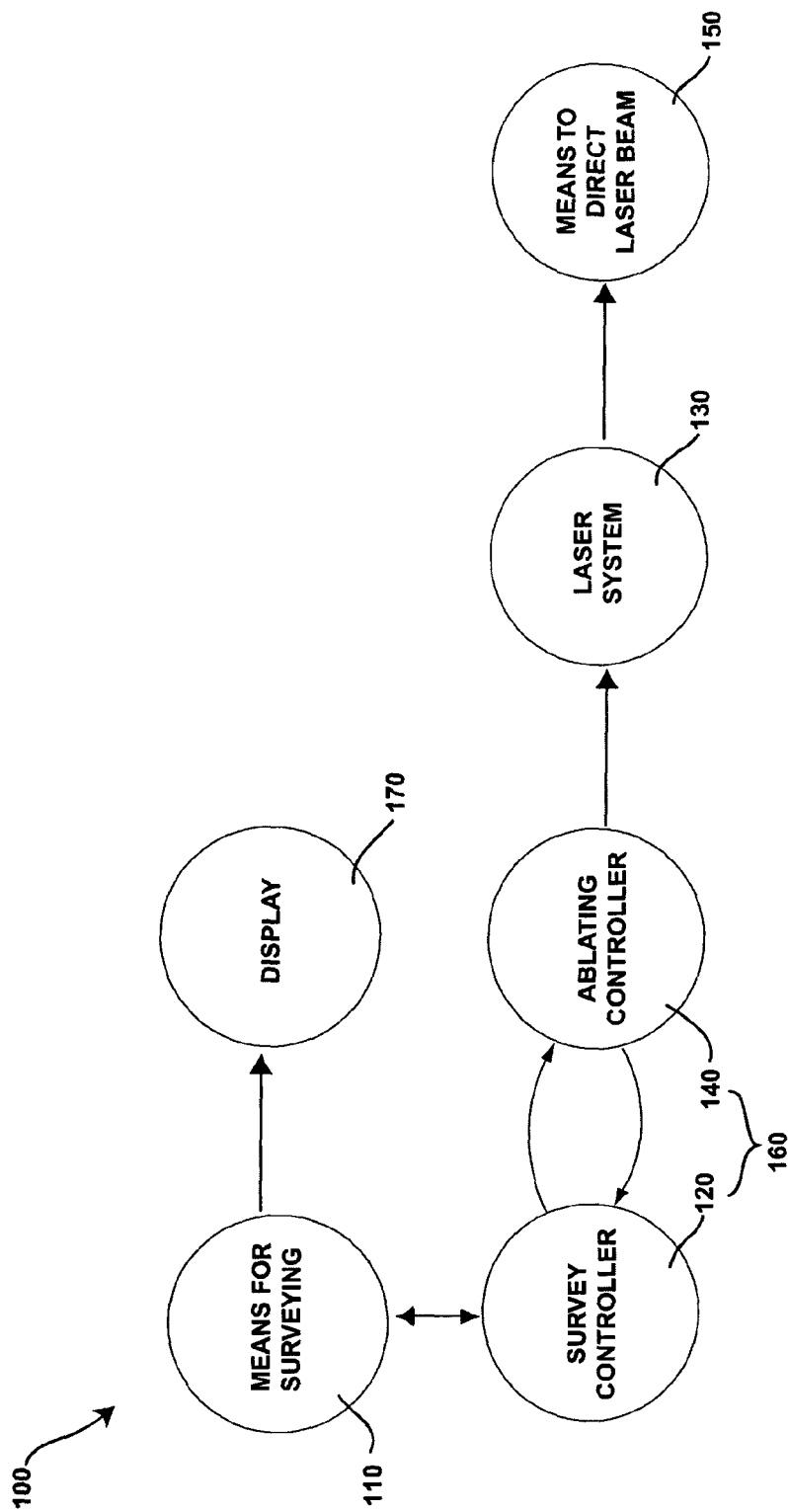
FIG. 3 shows a functional arrangement of a system according to the present invention.

Referring to FIG. 3, which shows a system according to the present invention. The system (100) comprises a means for surveying (110) to survey the lens and the structures anterior to the lens, a laser system (130) for ablating, within the lens, a means for monitoring and controlling (160) the photo ablating process in real time and a means to direct a laser beam (150). The means for monitoring and controlling (160) comprises a surveying controller (120) and an ablating controller (140). According to preferred embodiment of the invention, the surveying controller (120) and the ablating controller (140) are in feedback loop.

Figure 4:
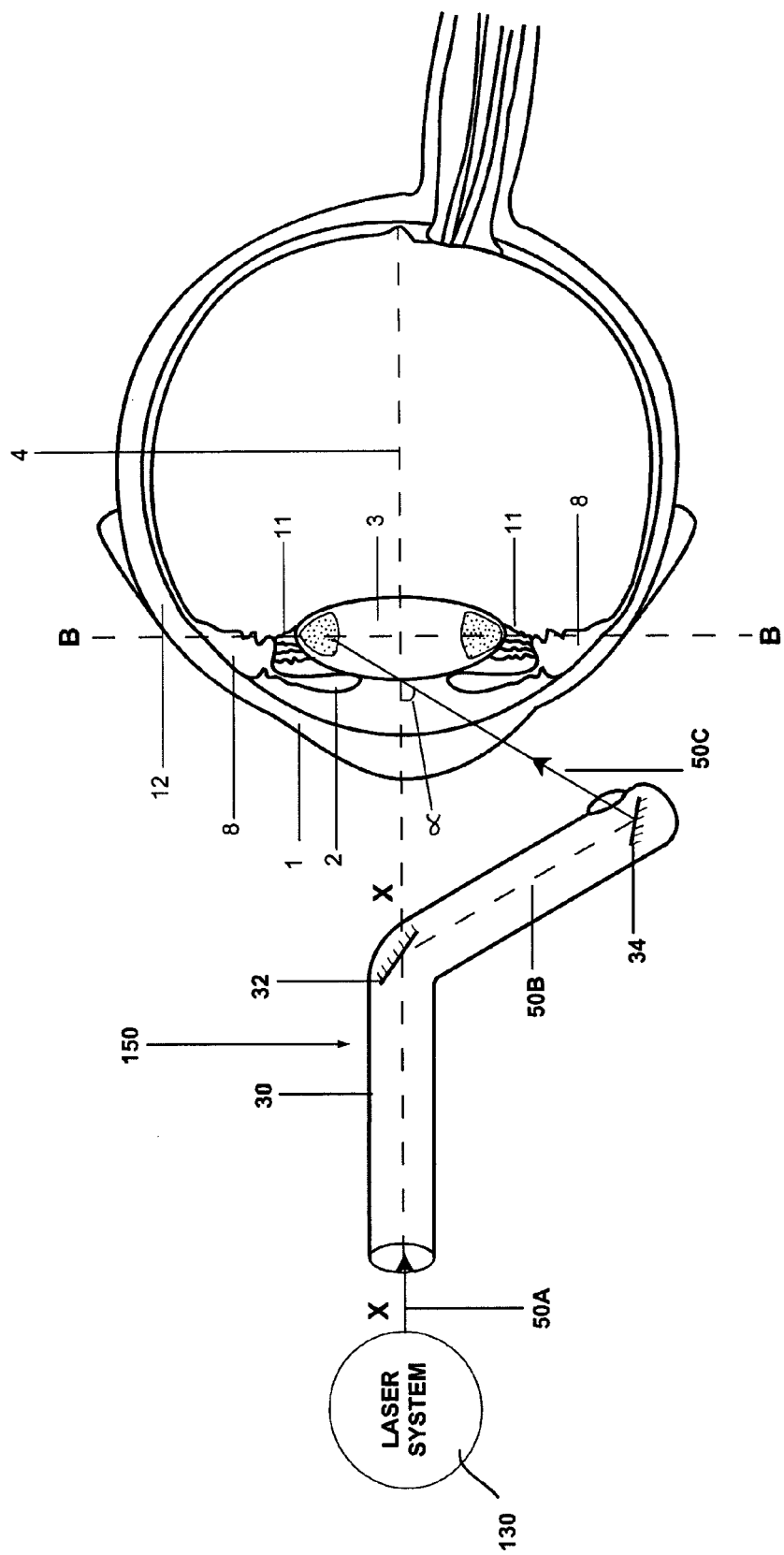
FIG. 4 shows a laser beam directed by a means to direct of the system according to the present invention.

FIG. 4 shows a means to direct a laser beam (150) according to the present invention. The means to direct a laser system can be adapted fixedly or removably on the laser-emitting source of the laser system. The means to direct (150) comprises at least two mirrors (32, 34) adapted periscopically within an articulated tube (30). The tube (30) is adapted on the laser-emitting source (not shown) of the laser system (130) to receive the laser beam incidentally emitted by the laser system (130) and is rotatable about a central axis (X-X) of the laser-emitting source. The first mirror (32) reflects the incidental laser beam (50A) emitted by the laser emitting source towards the second mirror (34) and the second mirror (34) diverts the reflected laser beam (50B) shown as (50C) towards a point at a predetermined angle ($\alpha$) within a selected zone (20) in a coronal plane for photoablation within the lens behind the iris. According to the invention one or both the mirrors can be adapted pivotally in order to change the angle of the laser beam. Preferably, second mirror (32) is adapted pivotally to direct the laser beam. Further, the distance of the means to direct from the eye can be used to change the position of the photoablation. The means to direct directs/diverts the laser beam in an angle range of 15-75° to the central axis (x-x) of the laser-emitting source.

According to the present invention, the laser system emits a laser beam having pulse duration not exceeding 500 femto-second and fluence between 3-15 Joules per sq. cm with a repetition rate is in excess of 100 Kilo Hz. The laser beam used for photo-ablation according to the present invention has a diameter between 4 to 100 microns and preferably has a diameter between 4 to 20 microns. This short duration laser beam has ability to convert lens protein into plasma, which gently diffuses away and out of the lens.

According to the present invention, the means for surveying is a surveying coherence optical tomography system such as Optical Coherence Tomography system (OCT) including ultrasound imaging, magnetic resonance imaging, electromagnetic radiation based on tomographic or photonic imaging apparatus and the surveying process includes preparing three-dimensional image of the lens and calculating the mass of the protein to be photoablated.

According to the method of the present invention, the means for surveying emits a scanning beam (not shown) along the central axis of the presbyopic lens to scan and analyze the lens for producing a three-dimensional image of the lens and the structures anterior to the lens with the help of software and to calculate volume of the lens-proteins to be removed for re-establishing the accommodation of the lens. The three-dimensional image can be view on a display (170) during surgery process. The surveying procedure is performed in real time to allow monitoring and feedback for the subsequent step. The means for monitoring and controlling of the system uses this image to compute the positioning, movement and control the laser system in real time.

According to the present invention the volume of the lens to be removed is calculated by formula I:

$$\chi \pi r^2 \quad \text{Formula I}$$

Wherein
$\chi$=growth rate of the lens per year
r=radius of the normal lens.

After surveying, a middle coronal plane of the lens is defined and the lens is divided in number of parallel coronal planes to the middle coronal plane carrying out ablation. Generally, distance between the selected two adjacent coronal planes is 20 microns and the distance of the first coronal plane from anterior side and the last coronal plane from the posterior side of the lens are generally at least 50 micron. Once the lens is divided into the parallel coronal planes, a zone is selected in a coronal plane behind the iris to perform the photoablation.

Figure 1:
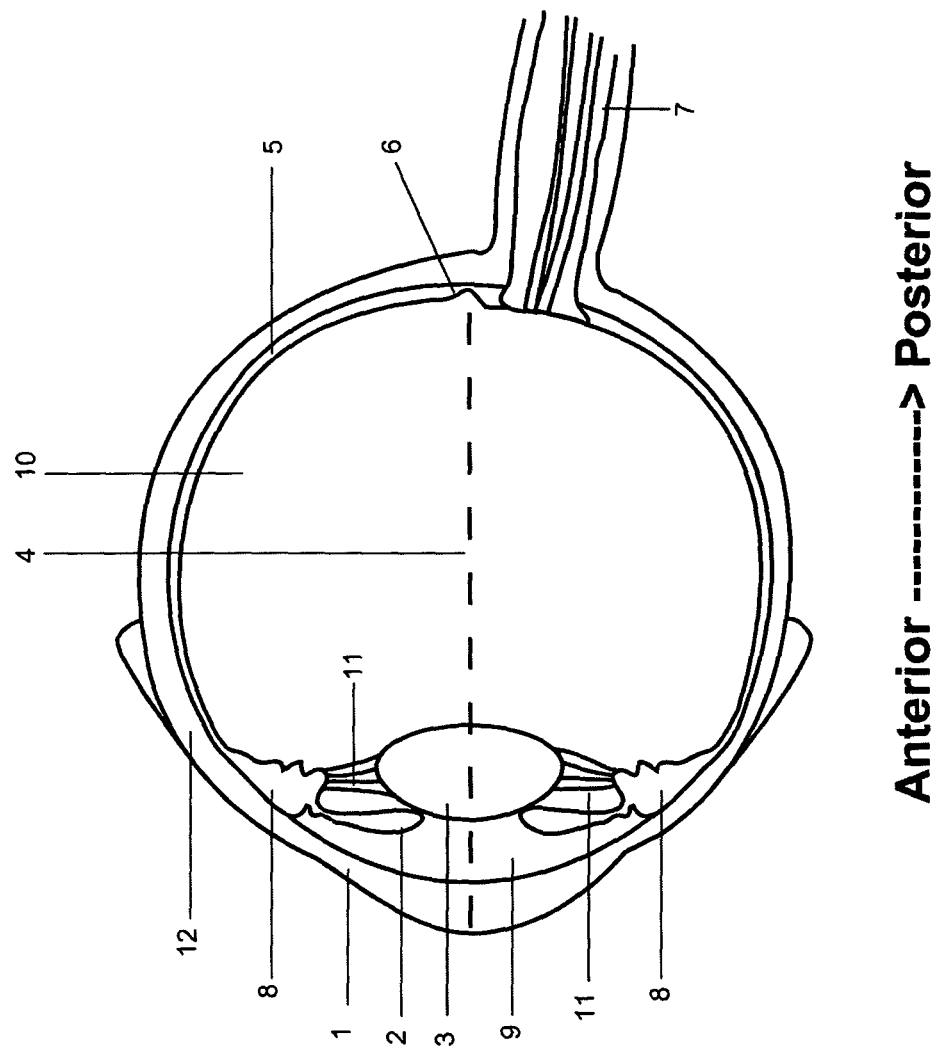
FIG. 1 shows a cross-sectional view of the eye showing gross anatomy of the eye.
Figure 2:
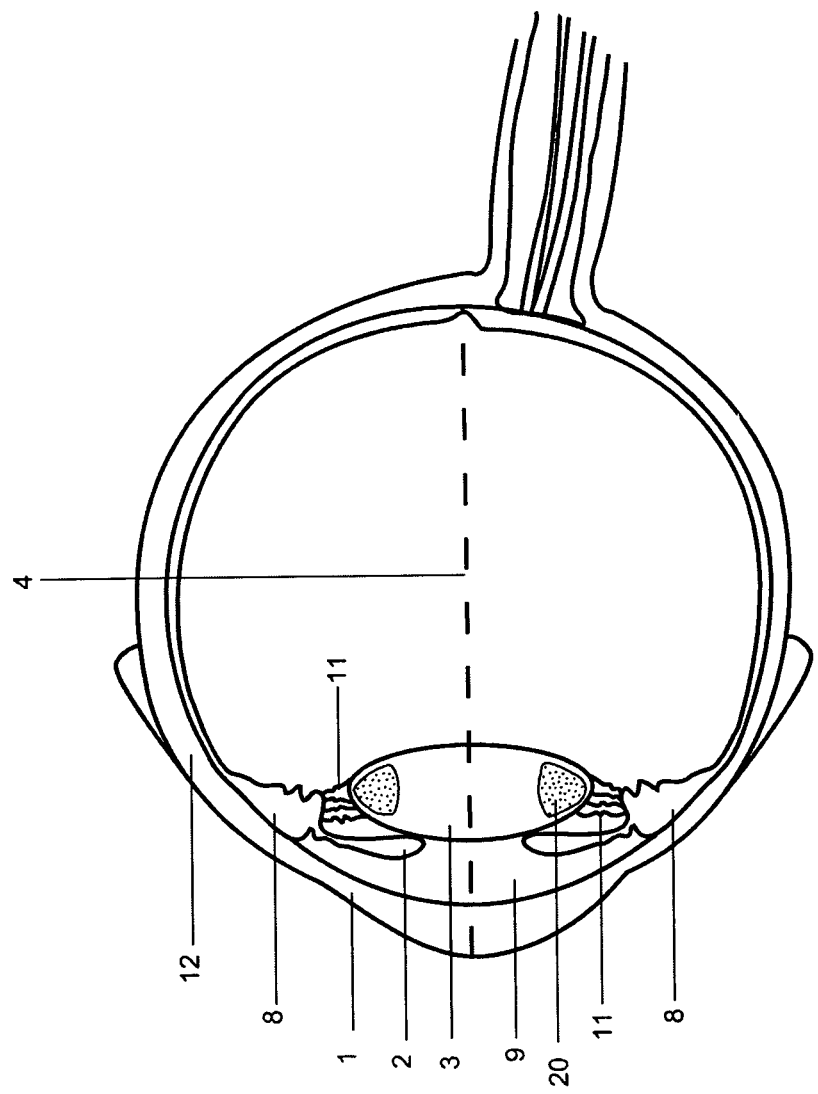
FIG. 2 shows a cross-sectional view of a presbyopic eye along with the ablation zone according to the present invention.

According to the Inventor, the zone(s) is selected within the lens behind the iris because it is most effective means of reducing coronal (equatorial) diameter of the lens, and also this zone is safe to remove the volume of the proteins behind the iris. According the Inventor, as the lens protein has firm gel-like properties, these properties of the proteins limits the ability of the lens to redistribute the volume within the lens capsule, therefore, removing the volume of the lens proteins from just anywhere may not be effective always to re-establish the accommodation of the lens means a specific volume of proteins must be required to remove from specific sites for desired outcome. Therefore, the inventor suggested removing the mass of the protein behind the iris and particularly near the equatorial region of the lens to reduce the dimension of the ocular plane, which results in decrease in the dimensions of the lens at a faster rate restoring the accommodation of the lens. Preferable zone according to the Inventor is a region at least 50 micron away from the equator of the lens within the lens and 2 mm away from the central axis of the lens. A presbyopic lens with preferable ablating zones (20) behind the iris (2) within the lens according to the present invention is shown in FIG. 2. As shown in FIG. 2, this zone is generally of doughnut/toroidal shape. Further, the inventor also suggests using oblique beam for ablation to avoid harm to the retina near the macula.

After the selection of the zone, photoablation is performed under the control of the ablating controller and surveying controller within the selected zone to covert the lens proteins in the plasma in order to reduce the diameter of coronal planes. The reduction in the diameter of the coronal planes near the equatorial region of the lens results in reduction in the diameter and thickness of the lens at sub-ciliary region of the eye which results decrease in circumlental crowding in the sub-cialiary region of the eye including crowding of the zonules and regaining tension of zonular fibres thereby re-establishing accommodation in the eye of the ocular lens.

According to the present invention, for photoablation, a coronal plane is selected. Generally, posterior coronal plane is selected first and photoablation is carried out in the planes toward the anterior side of the lens as per the requirement that is volume of the lens proteins to be removed. Once the coronal plane is selected, the central axis (X-X) of the laser-emitting source is matched with the central axis (4) of the lens as shown in FIG. 4 and a laser beam is emitted towards the selected zone by changing the direction. The direction of the laser beam is changed by passing the incidental laser beam through the means to direct (150). As shown in FIG. 4, the laser beam (50A) incidentally emitted by the laser system falls on the first mirror (32). The first mirror (32) reflects the laser beam (50B) towards the second mirror (34). The second mirror (34) diverts the reflected laser beam (50b) at a predetermined angle towards the selected point in the coronal plane within the zone behind the iris to perform spot photoablation behind the iris within the zone. The laser beam directed by the second mirror is shown in FIG. 4 as 50C and is called herein the disclosure as oblique beam). By rotating the means to direct about central axis of the lens, multiple photoablation spots are performed in circular way in the selected coronal plane behind the iris in the zone selected within the lens.

According to the present invention, the size of the spot of the photoablation created depends upon the diameter of the laser emitted. The preferable size of the spot according to the present invention is 10 micron. Further, a distance between the two adjacent photoablated spots in the same coronal plane or parallel coronal planes is about at least 10 microns. Depending upon the volume of the lens proteins to be removed, the multiple circular spot-photoablation in toroidal way around the axis of the lens can be performed in the same plane and/or planes i.e. anterior or posterior coronal planes parallel to the selected plane.

According to the present invention, the number of the spot photoablation to be done depends upon volume of the lens to be removed for one-year reversal, diameter of the lens beam and amount of the total energy to be delivered to the lens.

According to the present invention, the distance of the further selected plane and the selected plane is preferably about 20 microns and the distance between the photoablation spots between the adjacent parallel planes is preferably about 10 microns. In this way millions of the photoablation spots can be created to re-establish the accommodation of the lens within the eye.

Figure 5:
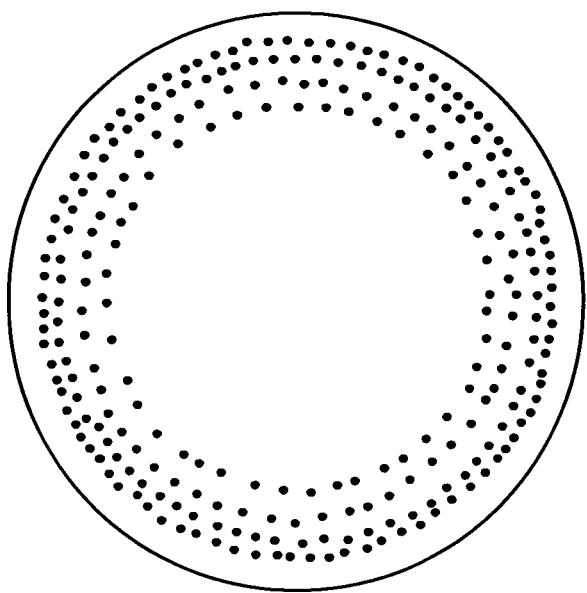
FIG. 5 shows a magnified view of the photoablated coronal plane at the line B-B as shown in FIG. 4
Figure 6:
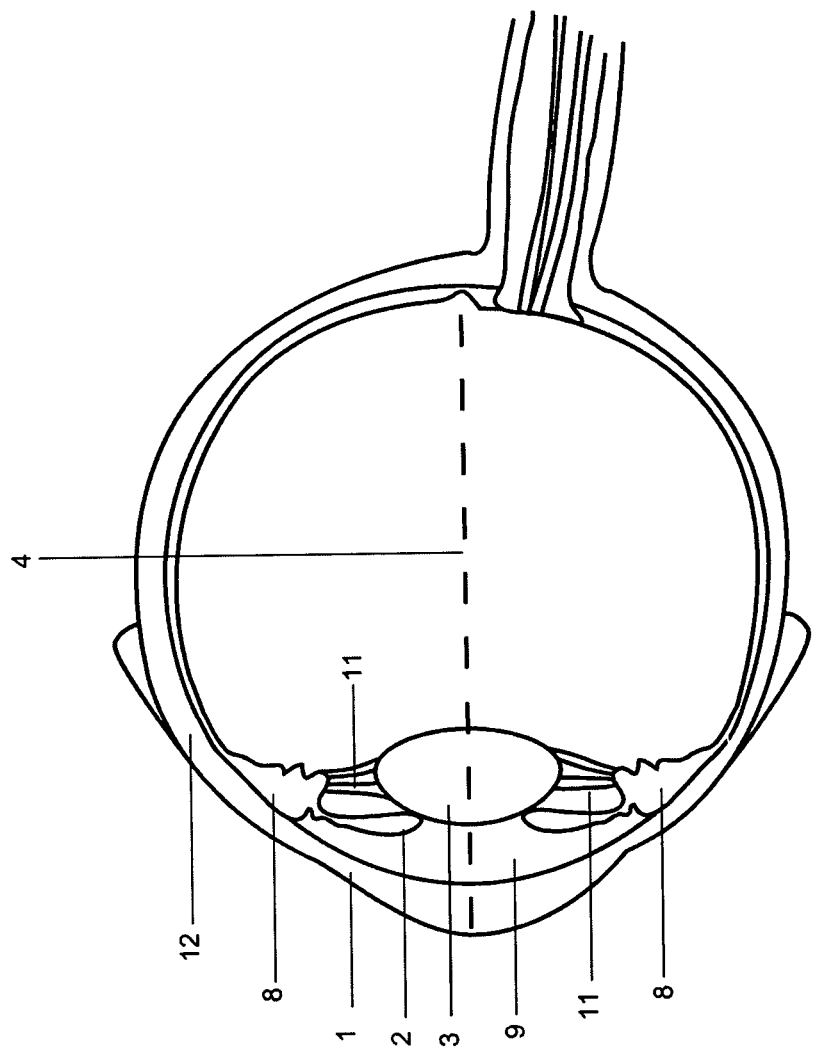
FIG. 6 shows decrease in dimension/coronal diameter of presbyopic lens as shown in FIG. 2 after the ablation according to the present invention in the preferred zones.

The spot photoablation takes place behind the iris within the eye due to disruption of covalent bonds between the lens proteins caused by the pulsing of the high-energy short-duration laser beam causing result in the formation of the microscopic plasma within the lens. The plasma at photoablation spots gently diffuses into the surrounding tissues and subsequently diffuses out of the eye. The diffusing process is high enough as the ablation performed in the present invention near the equator which also effects the re-distribution of the lens proteins with the help of elasticity of the lens capsule helping curing fastest causing reduction in the coronal diameter and thickness at sub-equatorial region of the lens along with reduction in circumlental crowding in the sub-cialiary region of the eye including crowding of the zonules. As the coronal diameter of the lens decreases, the zonules become more and more responsive to the ciliary muscle contraction. The enhancement/improvement of the ability of the ciliary muscle to constrict and relax via zonular ligaments by reducing the coronal diameter of the lens serves to shape the crystalline lens to appropriate optical configuration for focusing light rays from the objects onto retina, and consequently lead to restoration of accommodation ability of eye. FIG. 6 shows the reduction in the diameter of the lens shown in FIG. 5 after photoablation at the preferred zones according to the present invention.

The surveying controller and the ablating controller acting in feedback loop monitor photoablation process to control the laser system. When the ciliary muscles restore the optimal response from the lens of sufficient elasticity, the surveying controller signals to the ablating controller to terminate the ablation process.

The ablation process can be terminated at any time and vision can be tested for proper accommodation at any time and ablation can be repeated as per the requirement and can be carried out in one or more sittings depending upon the amount of the energy supplied to the eye in one sitting.

As the present invention uses laser beam having short duration pulse with high energy such as laser beam having pulse duration not exceeding 500 femto second and fluence between 3-15 Joules per sq. cm with a repetition rate is in excess of 100 KHz, conduction of heat takes place or generation of shockwave within the lens is substantially negligible. Therefore, no thermal or shockwave injury takes place to the adjacent tissues of the lens. Further, one of the advantages of the present invention is that present invention uses oblique laser beam for ablation, which substantially avoids damages of the retina near the macula.

The nouns first and second are referred in the description for the purpose of the understanding and nowhere limit the invention. Further, the means to direct can be rotate in clockwise or anticlockwise direction. In present invention, the rotation of the means to direct is important and not the direction of rotation. While the present invention has been described with respect to certain preferred embodiments, it will be apparent to those skilled in the art that various changes and modification may be made without departing from the scope of the invention as defined in the following claims:

The invention claimed is:

1. A method for restoring accommodation of a lens having vision defect/problem including presbyopia in eye, said method comprising steps of:
    surveying a lens to be treated;
    establishing accommodation amplitude for the lens;
    estimating actual accommodation amplitude for the lens and determining the volume of the lens proteins to be photoablated;
    dividing the lens into parallel coronal planes;
    locating a zone for photoablation within the lens behind the iris;
    selecting a coronal plane for photoablation;
    directing an incidental laser beam obliquely at a predetermined angle towards the coronal plane behind the iris to bring out a spot photoablation within the selected zones behind the iris; and
    performing plurality of spot photoablation in substantially circular way on the coronal plane behind the iris within the selected zone thereby reducing the coronal diameter and thickness at sub-equatorial region of the lens causing reduction in circumlental crowding in the sub-cialiary region of the eye including crowding of zonular fibers resulting tensing of zonular fibres thereby re-establishing accommodation in the eye of the ocular lens.

2. A method as claimed in claim 1 further comprising step of selecting further coronal plane anterior or posterior to the said coronal plane for photoablation behind the iris and photo-ablating in toroidal way in the selected zone depending on volume of the lens proteins to be removed.

3. A method as claimed in claim 2 wherein the further coronal plane is selected anterior to the photoablated coronal plane.

4. The method as claimed in claim 2 wherein distance between the two adjacent coronal planes is about 20 microns.

5. A method as claimed in claim 1 or 2 wherein the photo-ablating zone is at least 50 microns within the lens away from the equator of the lens and 2 mm from the central axis of the lens.

6. A method as claimed in claim 1 wherein the photoablation is carried from posterior to anterior.

7. A method as claimed in claim 1 wherein directing incidental laser beam obliquely step comprises steps of matching central axis of a laser system with the central axis of the lens; and
directing laser beam and pulsing the laser beam on periscopically arranged mirrors to direct laser beam obliquely toward the zones selected behind the iris.

8. A method as claimed in claim 1 or 7 wherein the laser beam is directed obliquely at an angle between 15 and 75 degrees to carry photoablation within the lens behind the iris of the eye.

9. A method as claimed in claim 1 wherein the zones to be photoablated are selected near the edge or equator of the lens and/or in the vicinity of zonules.

10. A method as claimed in claim 1 wherein selecting a coronal plane at least 50 microns away from the anterior of the lens.

11. A method as claimed in claim 1 wherein distance between the two adjacent photoablated spots in the same coronal plane or parallel coronal planes is about at least 10 microns.

12. A method as claimed in claim 1 wherein the laser beam emitted has pulse duration of laser beam not exceeding 500 femto-second.

13. A method as claimed in claim 1 wherein a fluence of the laser beam is between 3-15 Joules per sq. cm and a repetition rate is in excess of 100 Kilo Hz.

14. A method as claimed in claim 1 wherein the laser beam emitted has a diameter between 4 to 100 microns.

15. A method as claimed in claim 1 wherein laser beam emitted has diameter between 4 to 20 microns.

16. A method as claimed in claim 1 wherein volume of the lens proteins to be removed is calculated for one year by formula I:

$$\chi \pi r^2 \qquad \text{Formula I}$$

wherein
$\chi$=growth rate of the lens per year
r=radius of the normal lens.

17. A method for restoring accommodation of a presbyopic lens in eye, said method comprising steps of:
    obtaining a three-dimensional image of the lens;
    selecting a zone for ablating behind iris of the eye;
    ablating the said zone by passing a laser to reduce the coronal diameter and thickness at sub-equatorial region of the lens for re-establishing accommodation in the eye of the ocular lens.

18. A method as claimed in claim 17 wherein the zones to be photoablated are selected near the edge or equator of the lens and/or in the vicinity of zonules.

19. A method as claimed in claim 17 wherein said three-dimensional image is obtained by surveying coherence optical tomography system including optical coherence tomography system (OCT) including ultrasound imaging, magnetic resonance imaging, electromagnetic radiation based on tomographic or photonic imaging apparatus.

20. A system for performing photoablation of a lens having vision defect/problem including presbyopia, said system comprising:
    a. a means for surveying the lens and anterior parts thereof for establishing and estimating actual accommodation amplitude for the lens and to select a zone for photoablation within the lens behind the iris;
    b. a laser system for ablating within the lens; and
    c. a means for monitoring and controlling the photoablation process in real time; and
    d. a directing means adapted rotatably on the laser system for diverting a laser beam obliquely at a predetermined angle with the central axis within the lens behind the iris for photo-ablating the selected zone behind the iris to re-establish accommodation in the eye of the ocular lens, said directing means comprises an articulated arm tube rotatable about an axis and at least two mirrors adapted periscopically in the said tube wherein first mirror receives the incident laser beam and directs towards the second mirror, which reflect the laser beam obliquely towards the zone selected behind the iris for photoablation.

21. The system as claimed in claim 20 wherein the second mirror is adapted pivotally movable to direct the laser beam at the selected zone.

22. The system as claimed in claim 20 wherein the directing means directs the laser beam at an angle between 15 and 75 degrees.

23. The system as claimed in claim 20 wherein the laser beam emitted has pulse duration of laser beam not exceeding 500 femto-second.

24. The system as claimed in claim 20 wherein a fluence of the laser beam is between 3-15 Joules per sq. cm and a repetition rate is in excess of 100 Kilo Hz.

25. The system as claimed in claim 20 wherein the laser beam emitted has a diameter between 4 to 100 microns.

26. The system as claimed in claim 20 wherein the laser beam has a diameter about 4 to 20 microns.

27. The system as claimed in claim 20 wherein a means for surveying is a surveying coherence optical tomography system including optical coherence tomography system (OCT) including ultrasound imaging, magnetic resonance imaging, electromagnetic radiation based on tomographic or photonic imaging apparatus.

* * * * *